US009775506B2

(12) United States Patent
Burlina et al.

(10) Patent No.: US 9,775,506 B2
(45) Date of Patent: Oct. 3, 2017

(54) SYSTEM AND METHOD FOR DETECTING AND CLASSIFYING SEVERITY OF RETINAL DISEASE

(71) Applicant: The Johns Hopkins University, Baltimore, MD (US)

(72) Inventors: Philippe M. Burlina, North Bethesda, MD (US); David E. Freund, Columbia, MD (US); Srihari Kankanahalli, Columbia, MD (US); Neil M. Bressler, Owings Mills, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 35 days.

(21) Appl. No.: 14/437,777

(22) PCT Filed: Jul. 10, 2013

(86) PCT No.: PCT/US2013/049971
§ 371 (c)(1),
(2) Date: Apr. 22, 2015

(87) PCT Pub. No.: WO2014/074178
PCT Pub. Date: May 15, 2014

(65) Prior Publication Data
US 2015/0265144 A1  Sep. 24, 2015

Related U.S. Application Data

(60) Provisional application No. 61/724,010, filed on Nov. 8, 2012.

(51) Int. Cl.
*A61B 3/14* (2006.01)
*A61B 3/00* (2006.01)
(Continued)

(52) U.S. Cl.
CPC .............. *A61B 3/0025* (2013.01); *A61B 3/10* (2013.01); *A61B 3/102* (2013.01); *A61B 3/12* (2013.01);
(Continued)

(58) Field of Classification Search
CPC .... A61B 3/10; A61B 3/12; A61B 3/14; A61B 5/7275; A61B 5/7246; A61B 3/102;
(Continued)

(56) References Cited

U.S. PATENT DOCUMENTS

2002/0052551 A1* 5/2002 Sinclair .............. A61B 5/02014
600/476
2006/0257017 A1 11/2006 Luo
(Continued)

OTHER PUBLICATIONS

International Search Report and Written Opinion of PCT/US2013/049971.

*Primary Examiner* — Scott J Sugarman
*Assistant Examiner* — Mustak Choudhury
(74) *Attorney, Agent, or Firm* — Venable LLP; Henry J. Daley

(57) ABSTRACT

A method of detecting, and classifying severity of, a retinal disease using retinal images includes at least one of receiving, retrieving or generating reference data that includes information concerning occurrences of key image features for each of a plurality of retinal disease and disease severity conditions; receiving a retinal image of an individual; processing the retinal image of the individual to identify occurrences of each of a plurality of distinguishable image features throughout at least a region of interest of the retinal image; identifying which ones of the identified occurrences of the plurality of distinguishable image features of the retinal image of the individual correspond to the key image features of the reference data; calculating, based on the identifying, a number of occurrences of each of the key image features in the retinal image of the individual; and determining at least one of a likelihood of a presence of a retinal disease or a likelihood of developing a retinal disease based on a comparison of the number of occurrences of each
(Continued)

of the key image features in the retinal image of the individual to the reference data.

31 Claims, 6 Drawing Sheets

(51) Int. Cl.
    *A61B 3/10*     (2006.01)
    *A61B 3/12*     (2006.01)
    *A61B 5/00*     (2006.01)
    *G06T 7/00*     (2017.01)

(52) U.S. Cl.
    CPC .............. *A61B 3/14* (2013.01); *A61B 5/7246* (2013.01); *A61B 5/7264* (2013.01); *A61B 5/7275* (2013.01); *G06T 7/0012* (2013.01); *G06T 2207/20076* (2013.01); *G06T 2207/30041* (2013.01)

(58) Field of Classification Search
    CPC ... A61B 3/0025; A61B 5/7264; G06T 7/0012; G06T 2207/30041; G06T 2207/20076
    USPC ......... 351/202–211, 221, 246; 382/128, 159, 382/275; 600/301
    See application file for complete search history.

(56) References Cited

U.S. PATENT DOCUMENTS

| | | | |
|---|---|---|---|
| 2010/0041963 A1* | 2/2010 | Haider | G06T 7/0012 600/301 |
| 2011/0026789 A1* | 2/2011 | Hsu | G06K 9/0061 382/128 |
| 2011/0242306 A1 | 10/2011 | Bressler et al. | |
| 2012/0237096 A1 | 9/2012 | Tobin et al. | |

* cited by examiner

SYSTEM AND METHOD FOR DETECTING AND CLASSIFYING SEVERITY OF RETINAL DISEASE

CROSS-REFERENCE OF RELATED APPLICATION

This is a national stage application under 35 U.S.C. §371 of PCT/US2013/049971 filed Jul. 20, 2013, the entire contents of which are incorporated herein by reference and this application claims priority to U.S. Provisional Application No. 61/724,010 filed Nov. 8, 2012, the entire content of which is hereby incorporated by reference.

BACKGROUND

1. Field of Invention

The field of the currently claimed embodiments of this invention relates to systems and methods for detecting and classifying the severity of retinal disease.

2. Discussion of Related Art

Age-related macular degeneration (AMD) is the leading cause of blindness if left untreated throughout much of the western world for individuals over age 50[1]. Vision loss can occur from the advanced stage, which includes choroidal neovascularization (CNV) or geographic atrophy involving the center of macula. The advanced stage can lead to severely impaired central vision, impacting everyday activities[2]. In the United States, approximately 200,000 individuals over the age of 50 develop the advanced stage of AMD each year in at least one eye[3]. Left untreated, approximately 70% of these cases develop substantial vision loss in the affected eye within 2 years. Furthermore, of those patients who developed advanced AMD in only one eye, approximately half will develop the advanced stage in the other eye within 5 years, resulting in a high risk of developing legal blindness if left untreated[1].

Although there is no definitive cure for AMD, the Age-Related Eye Disease Study (AREDS) has suggested benefits of certain dietary supplements for slowing the progression of the disease from the intermediate stage to the advanced stage[4]. In addition, recent clinical trials of anti-vascular endothelial growth factor (VEGF) for treating CNV can eliminate a substantial proportion of cases which otherwise would progress to the advanced stage[5]. The better the visual acuity at the onset of anti-VEGF therapy, the greater is the chance of avoiding substantial visual acuity impairment or blindness[2]. Thus, it is critical to identify in a timely manner those individuals most at risk for developing advanced AMD, specifically, individuals with the intermediate stage of AMD.

The following drusen classification method was adopted by the AREDS Coordinating Centers[6]: large drusen are defined as those that exceed 125 microns in diameter (the average size of a retinal vein at the optic disk margin), small drusen are defined as those with diameters less than 63 microns, and medium-sized drusen are defined as those with diameters in the range between 63 and 125 microns. The intermediate stage of AMD is characterized by the presence of numerous medium-sized drusen, or at least one large druse within 3000 microns of the center of the macula (FIG. 1). While a dilated ophthalmoscopic examination at least every 2 years to detect asymptomatic conditions potentially requiring intervention, such as the intermediate stage of AMD, is recommended by the American Academy of Ophthalmology [AAO PPP], the presence of drusen often causes no symptoms and therefore no motivation for an individual to seek examination by an eye care provider to detect an asymptomatic intermediate stage.

Currently, ophthalmoscopy of the retina by trained health care providers (including ophthalmologists) or evaluation of fundus photographs by trained graders (including ophthalmologists) remains the most effective method to identify the intermediate stage of AMD[1]. However, grading fundus images manually by a grader can be a tedious process requiring the expertise of an adequately trained health care provider or extensively trained fundus photograph grader to understand the varying patterns recognized by an ophthalmologist[7]. Furthermore, access to an ophthalmology health care provider at least every 2 years to detect the intermediate stage of AMD after age 50 can be challenging for many health care environments. Therefore, there is a need for automated visual diagnostic tools to facilitate the detection of the intermediate stage AMD among a large pool of the at-risk population. As an example of the potential health care burden of this issue, in 2010, in the United States, there were about 98 million individuals over the age of 50 and this number is projected to increase to approximately 109 million by 2015[8].

SUMMARY

A method of detecting, and classifying severity of, a retinal disease using retinal images according to an embodiment of the current invention includes at least one of receiving, retrieving or generating reference data that includes information concerning occurrences of key image features for each of a plurality of retinal disease and disease severity conditions; receiving a retinal image of an individual; processing the retinal image of the individual to identify occurrences of each of a plurality of distinguishable image features throughout at least a region of interest of the retinal image; identifying which ones of the identified occurrences of the plurality of distinguishable image features of the retinal image of the individual correspond to the key image features of the reference data; calculating, based on the identifying, a number of occurrences of each of the key image features in the retinal image of the individual; and determining at least one of a likelihood of a presence of a retinal disease or a likelihood of developing a retinal disease based on a comparison of the number of occurrences of each of the key image features in the retinal image of the individual to the reference data.

A computer-readable medium for detecting, and classifying severity of, a retinal disease using retinal images according to an embodiment of the current invention includes non-transitory computer-executable code which, when executed by a computer, causes the computer to at least one of receive, retrieve or generate reference data that includes information concerning occurrences of key image features for each of a plurality of retinal disease and disease severity conditions; receive a retinal image of an individual; process the retinal image of the individual to identify occurrences of each of a plurality of distinguishable image features throughout at least a region of interest of the retinal image; identify which ones of the identified occurrences of the plurality of distinguishable image features of the retinal image of the individual correspond to the key image features of the reference data; calculate, based on the identifying, a number of occurrences of each of the key image features in the retinal image of the individual; and determine at least one of a likelihood of a presence of a retinal disease or a likelihood of developing a retinal disease based on a comparison of the number of occurrences of each of the key image features in the retinal image of the individual to the reference data.

A system for detecting, and classifying severity of, a retinal disease according to an embodiment of the current invention includes a retinal scanner constructed to obtain retinal images of an individual, and a data processing system in communication with the retinal scanner. The data processing system is configured to at least one of receive, retrieve or generate reference data that includes information concerning occurrences of key image features for each of a plurality of retinal disease and disease severity conditions; receive a retinal image of the individual from the retinal scanner; process the retinal image of the individual to identify occurrences of each of a plurality of distinguishable image features throughout at least a region of interest of the retinal image; identify which ones of the identified occurrences of the plurality of distinguishable image features of the retinal image of the individual correspond to the key image features of the reference data; calculate, based on the identifying, a number of occurrences of each of the key image features in the retinal image of the individual; and determine at least one of a likelihood of a presence of a retinal disease or a likelihood of developing a retinal disease based on a comparison of the number of occurrences of each of the key image features in the retinal image of the individual to the reference data.

A method of detecting, and classifying severity of, a disease using physiological information according to an embodiment of the current invention includes at least one of receiving, retrieving or generating reference data that includes information concerning occurrences of key features for each of a plurality of disease and disease severity conditions; receiving physiological information of an individual; processing the physiological information of the individual to identify occurrences of each of a plurality of distinguishable features throughout at least a portion of the physiological information; identifying which ones of the identified occurrences of the plurality of distinguishable features of the physiological information of the individual correspond to the key features of the reference data; calculating, based on the identifying, a number of occurrences of each of the key features in the physiological information of the individual; and determining at least one of a likelihood of a presence of a disease or a likelihood of developing a disease based on a comparison of the number of occurrences of each of the key features in the physiological information of the individual to the reference data.

BRIEF DESCRIPTION OF THE DRAWINGS

Further objectives and advantages will become apparent from a consideration of the description, drawings, and examples.

DETAILED DESCRIPTION

Figure 1:
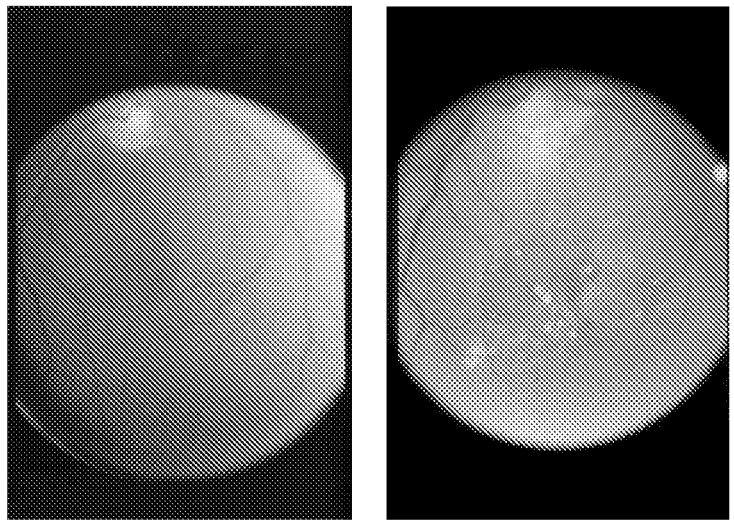
FIG. 1 shows examples of four fundus images with increasing AMD severity. Upper left: an AMD category 1 (no AMD). Upper right: an AMD category 2 (early AMD); Lower left: an AMD category 3 (intermediate AMD) with geographic atrophy not involving the center of the retina; Lower right: an AMD category 4 with evidence of both neovascularization and geographic atrophy (advanced AMD). As is seen in these images, the background retina can show variations in hue and the retinal fundus images may have various artifacts.
Figure 1:
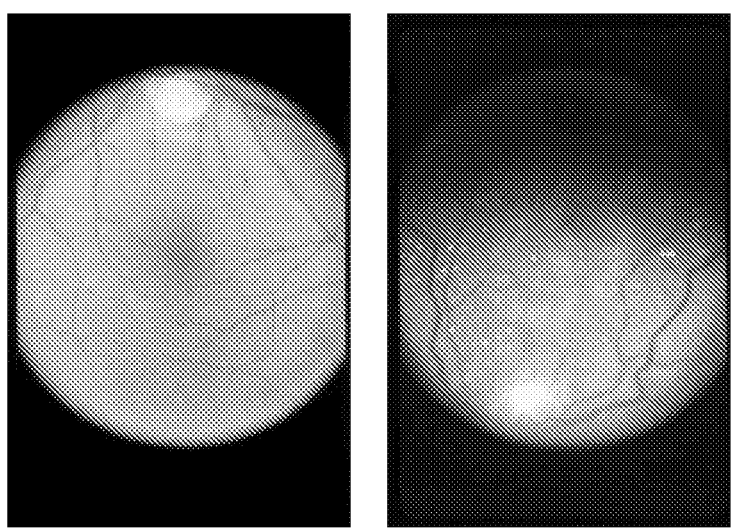

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

A substantial body of work has been devoted to the design of automated retinal image analysis (ARIA) algorithms. While ARIA algorithms for diabetic retinopathy or glaucoma are showing promise[9], less progress, in the opinion of the authors, has been made in the area of AMD. Some AMD detection methods require user intervention[10]. Recently, researchers have emphasized automated approaches by using adaptive equalization and wavelets[11]; employing mathematical morphology[12] on angiographic images; using adaptive thresholding[13]; exploiting probabilistic boosting approaches for the classification of non-homogeneous drusen textures[14]; using probabilistic modeling and fuzzy logic[15]; employing histogram normalization and adaptive segmentation[16]; exploiting texture discrimination and the intensity topographical profile[17]; utilizing morphological reconstruction[18]; employing a histogram-based segmentation method[19]; or, finally, using basic feature clustering to find bright lesions[20]. The interested reader is also referred to a recent review[9] of ARIA techniques.

Accordingly, some embodiments of the current invention provide methods to automatically process fundus images based on what can be conceptualized as a "visual words" approach in order to reliably detect evidence of AMD as well as accurately categorize its severity. Because the key factor in mitigating the worsening of AMD as it progresses from the intermediate stage to the neovascular form (and potentially, in the future, the geographic atrophic form) is early intervention, an application of the current invention can be to implement these algorithms in a public monitoring or screening system that is convenient and easily accessible to the general public. In essence, a system according to an embodiment of the current invention can analyze fundus images of an individual and quickly provide results including a grade of AMD severity and, if necessary, a recommendation to see an ophthalmologist for further evaluation, while avoiding false positive referrals.

A natural approach for finding and classifying AMD patients can include automatically finding drusen in fundus images (which is the aim of most of the above cited studies) and then using this to detect and classify the severity of AMD. This task may be difficult due to variations in patient specific appearance (variability in pigmentation of the choroid as well as drusen appearance within and across subjects), and it may be challenging to identify stable image features that are characteristic of drusen that can be used to build a robust classifier that will perform reliably over a large dataset. In contrast, an embodiment of the current invention uses an alternate strategy that focuses on classifying the entire fundus image, as a whole, as opposed to looking only for specific drusen or other lesions. The following will describe some concepts of the current invention in the context of an application to AMD detection and classification. The broad concepts of the current invention are not limited to the particular embodiments and examples.

Description of the Classification (Algorithm) Approach

Our approach to automatically classifying fundus images for AMD severity according to some embodiments of the current invention is built around the concept of visual words, also known as 'bag of words'[26]. This method was first used in the field of automated text classification. For example, suppose that the problem is to teach a computer to distinguish among newspaper articles on three news categories such as politics, sports, and business. The first step of this method is to determine what are the salient words, i.e., the method automatically selects keywords such as "president", "congress", "stocks", "campaign", "score", based on their importance. Next, a training phase is used in which the algorithm is provided example articles on the three news categories. During the training phase the algorithm is told under which category each article falls, and it infers the relative frequency (histograms) of all selected keywords in each article category. Given a corpus of new and uncategorized articles, the method would then categorize each article by looking at the frequency of each keyword it contains and selecting the category that has the closest histogram. This entire approach can be transposed to the problem of classifying retinal images into different categories of affected eyes, by substituting newspaper articles with fundus images and visual words with visual features computed in these fundus images.

Salient Visual Features.

Recently the visual words approach has been adapted by the computer vision community[26] to perform classification of images. As noted earlier, when used in this context, "salient visual features" take on the role of newspaper articles' keywords. Such features can be automatically characterized using robust feature detection methods such as SIFT (Scale Invariant Feature Transform) or SURF (Speeded Up Robust Feature). After all visual features in a set of training images have been detected, a K-means clustering approach can be used to find centroids of the features. K-means clustering is a classical technique used to partition a dataset into K different clusters and to find the clusters' centroid. The method is an iterative process that alternates between (a) ascribing data points to the cluster's centroids and relabeling them accordingly, and (b) re-computing the cluster's centroids given the newly formed clusters[27].

Next, the method reduces the number of all selected visual features across all training images to a smaller—user-specified—number of representative features forming a dataset of so-called "visual words". The set of training images is used once again to find the relative frequency of each of the visual words from images of each AMD category, forming prototypical visual words histograms that are characteristic of each AMD image category. As was described earlier, any new test image is then simply classified as follows: salient visual features are detected, a histogram is created, and the image is ascribed to the category whose visual word histogram most closely matches the visual word histogram of the test image. Other than selecting the number of visual words and providing images for training, the method does not need any additional input or supervision and is agnostic to the type of category or classification it is applied to.

Pre-Processing to Obtain Region of Interest.

Figure 2:
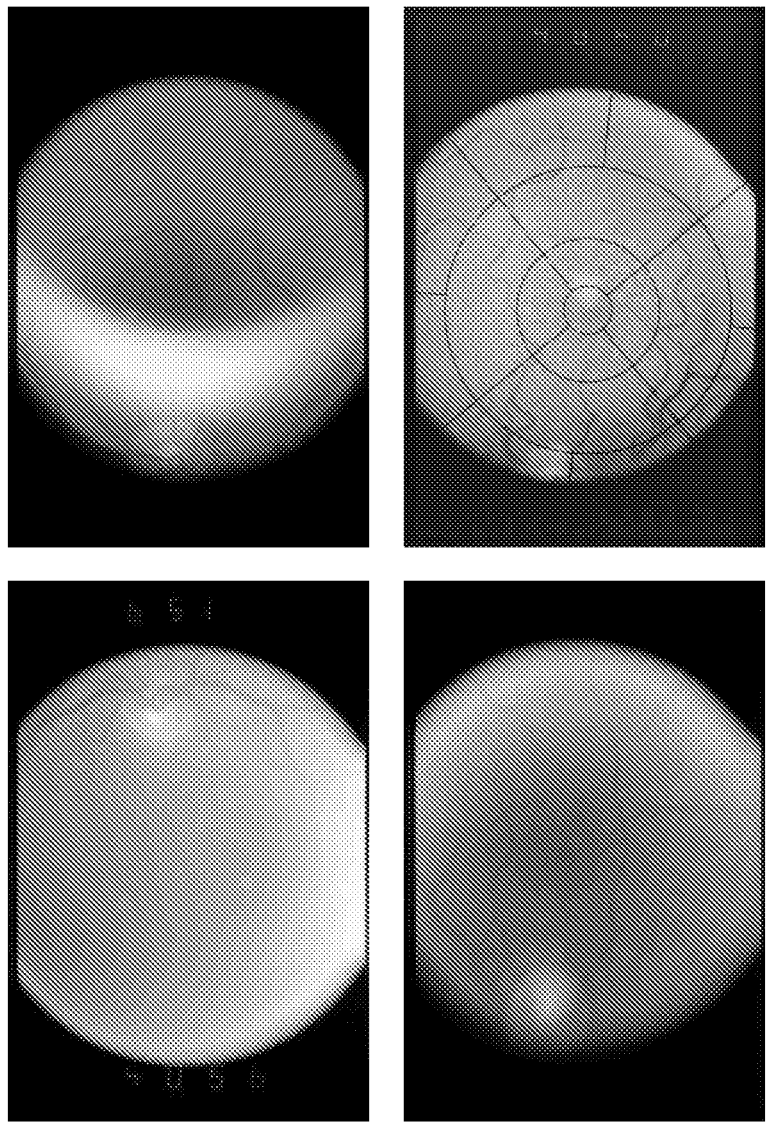
FIG. 2 shows examples of poor quality images: (top left) poor media, possible inadequate dilation, (top right) lateral misalignment, (lower left) poor focus, possible retinal layer separation—not the same focal plane for the lower arcade and the optic disc—and (lower right) grid still attached to fundus photograph.

Retinal images almost always have a black border that needs either to be avoided or eliminated. Within the AREDS database there are many images where the macula is off center, the border is lighter than pure black from flash or other photographic artifacts, red timestamps are placed on the border, or other artifacts are present besides the desired retinal area (see FIG. 2). To accurately and consistently obtain the region of interest (ROI), the following steps are used: i) the green channel of the RGB image is extracted and, to improve speed, resized to one-eighth size. ii) A 9×9 median filter is applied and then a binary image is created by thresholding (i.e. pixels above a prescribed value are set to 255 and those below to 0). iii) Next, a morphological opening and closing is applied with a round 3×3 structuring element, in order to eliminate background noise, timestamps, and other artifacts that are sometimes present in the AREDS images. iv) The minimum enclosing circle around all of the remaining points is found, and the inscribed square within that circle becomes the ROI where the rest of the algorithm is applied. v) The full image is then cropped to this square region and, to minimize processing time, resampled down to 700×700 resolution.

Preprocessing to Remove Large Background Intensity Gradient.

Images are affected by various degrees of intensity gradient variation that depends on the acquisition conditions. To remove this background intensity gradient, a new image is created by the following: (a) smoothing the green channel with a large median filter set to one-fourth of the image width, (b) subtracting the median filtered image from the original image's green channel, and (c) multiplying the result by 2 (to increase contrast) and adding 127.

Keypoint Detection and Feature Vector Descriptor Extraction.

To find keypoints (i.e. visual salient features), a SURF detector is used on the image resulting from the previous step. The SURF algorithm exploits a technique known as integral images to quickly find the image second derivative (the Hessian) and apply approximate Gaussian filters at multiple scales. Each scale is known as an octave, and each application of the Gaussian filter forms one layer. Here, keypoints are detected using ten octaves, three layers per octave, and a Hessian threshold of 600. The original image is then converted from the RGB color space to the L*a*b* color space[28] and a SURF descriptor for every keypoint is then computed for each L*a*b* channel. These 3 descriptors are then concatenated into one. This aids in classification because color is an important visual cue in finding retinal anomalies. Briefly, we remark here that the L*a*b color space is more representative of the way humans see and has several technical advantages over the more traditional RGB or HSV spaces. In particular, metrics for measuring distance between colors are essentially Euclidian. Furthermore, tones (Lightness) and colors (the a channel is green or magenta hue, and the b channel is blue or yellow hue) are held separately; thus, one can vary one without altering the other.[28]

Vocabulary Creation.

A vocabulary of visual words is created from the keypoint descriptors of the set of AMD-positive (i.e. category 3 and 4) images. The rationale for not including all images is that AMD-positive images contain all features (vessels, optical disk, artifacts) that are present in AMD-negative images plus drusen and other lesions (geographic atrophy, pigmentation, and other features.). A vocabulary of 100 visual words for two-class classification problems is used, and 300 visual words for three-class problems. The visual words are selected as the centroids found using K-means clustering. We emphasize here that this needs to be done only once; the same vocabulary is used for each subsequent run.[26]

Spatially-Dependent Histogram Generation.

To reflect the fact that AMD severity is graded by taking into account the location of the drusen and other AMD-related lesions, with the macular region taking a preponderant weight in the decision process (see FIG. 1 in[25]), the feature selection is region-dependent. This is based on subdividing the fundus image in pre-defined concentric regions. Several options are considered and compared in the Examples section below (see FIG. 3). Consequently, based on their distance from the center of the image (which corresponds approximately to the macula in most images), feature descriptors are grouped into several different sets and importance weights are applied to the histograms of each region based on distance of the region from the center, to emphasize regions close to the macula. Regional histograms are then concatenated back into a single large histogram for the entire image. This concatenated vector forms the final 'feature vector' used for classification.

Training and Testing.

The entire corpus of available images and their associated category labels is then used for training and testing. For each image, a final feature vector (visual word histogram) is generated once and for all. As is standard in machine learning applications, a N-fold cross validation approach is used. This consists of subdividing the dataset into N equally sized folds (i.e. subsets), using N−1 folds for training, and the remaining Nth fold for testing. Then, a random forest classifier is trained using the training dataset. The random forest algorithm uses the consensus of a large number of weak (only slightly better than chance) binary decision trees to classify the testing images into different severity classes.[29] For the two class problems the random forest consisted of 1,000 decision trees, whereas for the three class problem it consisted of 2,500.

Figure 4:
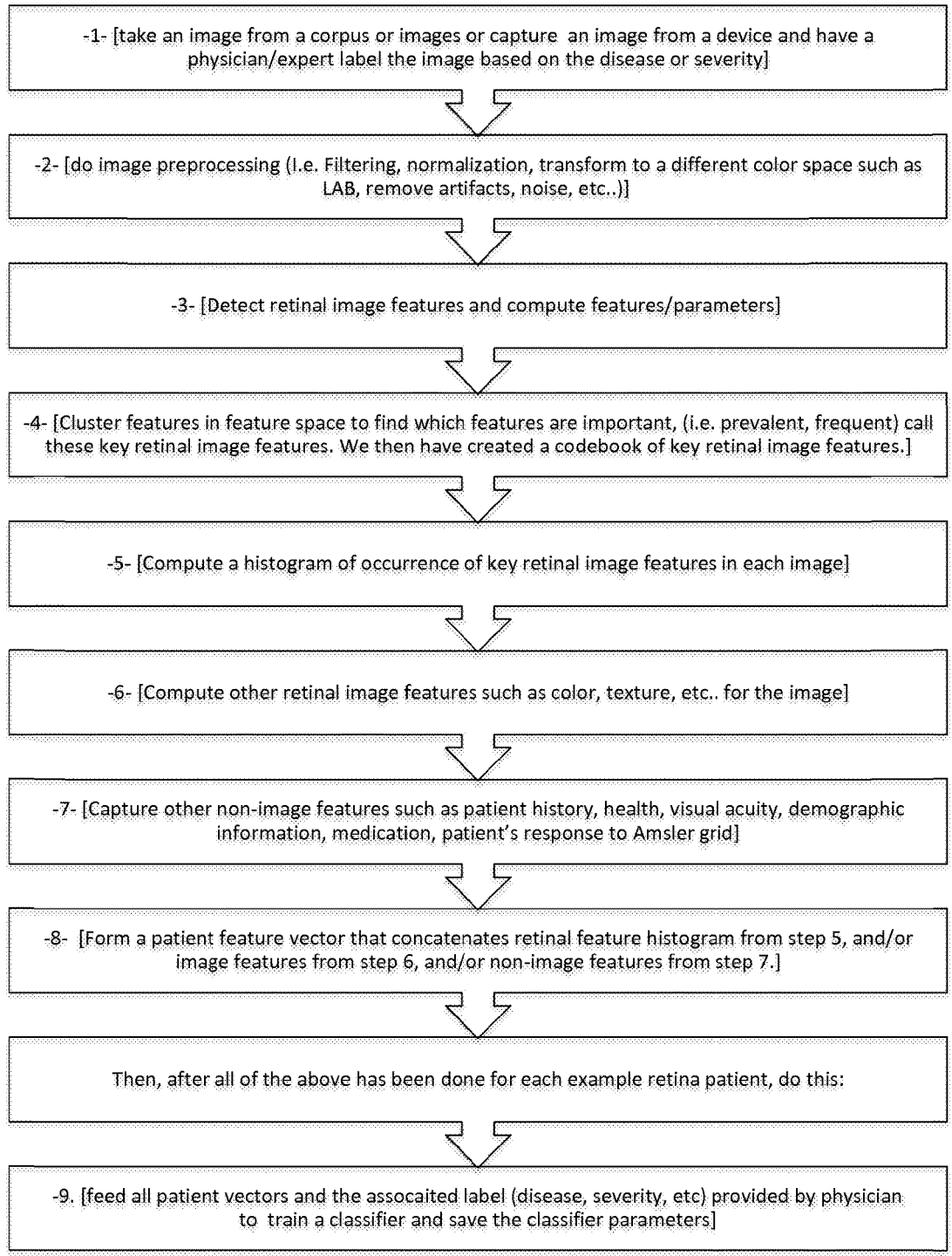
FIG. 4 shows a training phase flow chart according to an embodiment of the current invention.

FIG. 4 is a flowchart illustrating an embodiment of a training phase. In other words, visual word histograms for use as a reference are generated. The term "visual word" is used to help draw an analogy to the text example. The term "image feature" is used in the following to be more accurate. It should be understood that the above description with respect to "visual words" is intended to be included within the definition of "image features". Although all of the steps described in FIG. 4 can be included in some embodiments of the current invention, not all steps are always required. For example, some embodiments may include more or less of the processing summarized in item 2, or may even skip it altogether. Similarly, the processes in items 6 and/or 7 may be optionally included.

Figure 5:
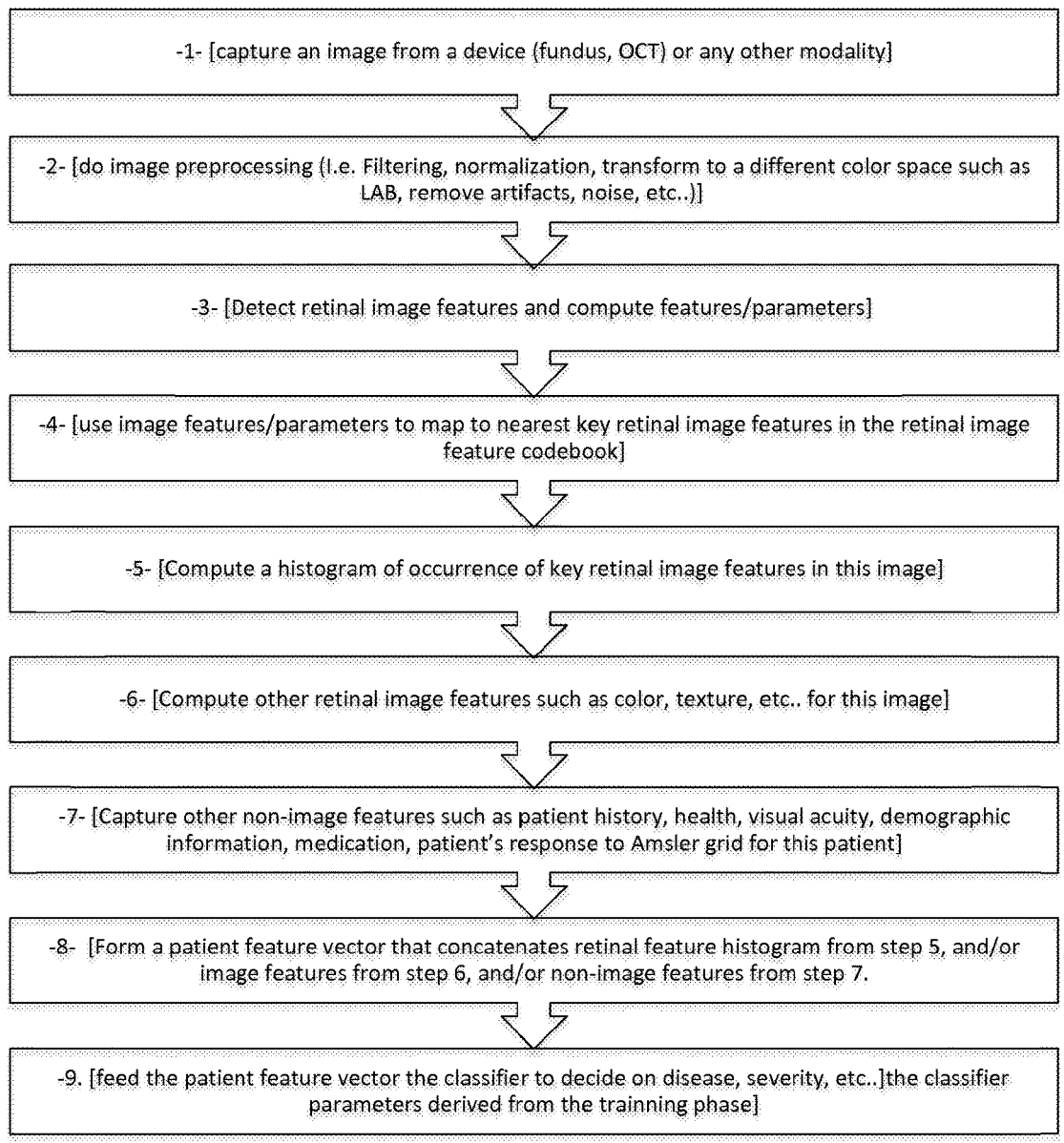
FIG. 5 shows a testing phase flow chart according to an embodiment of the current invention.

FIG. 5 is a flowchart illustrating an embodiment of a testing phase. Again, some embodiments can include all of the listed processes, while other embodiments can include a subset of the processes.

More generally, a method of detecting, and classifying severity of, a retinal disease using retinal images according to an embodiment of the current invention includes at least one of receiving, retrieving or generating reference data that includes information concerning occurrences of key image features for each of a plurality of retinal disease and disease severity conditions. The reference data can be generated according to the flow chart of FIG. 4, or variations of it as discussed above, for example. In some embodiments, the reference data may have been previously generated and the data could then be retrieved from data storage, for example, or could be provided by an external source such as by way of a data network, for example.

The method further includes receiving a retinal image of an individual. The retinal image can be from a fundus camera and/or an optical coherence tomography system, for example. However, retinal images from other systems can also be used according to other embodiments of the current invention.

The method further includes processing the retinal image of the individual to identify occurrences of each of a plurality of distinguishable image features throughout at least a region of interest of the retinal image. The image features can be the "image words" as described conceptually above, for example. The method further includes identifying which ones of the identified occurrences of the plurality of distinguishable image features of the retinal image of the individual correspond to the key image features of the reference data; calculating, based on the identifying, a number of occurrences of each of the key image features in the retinal image of the individual; and determining at least one of a likelihood of a presence of a retinal disease or a likelihood of developing a retinal disease based on a comparison of the number of occurrences of each of the key image features in the retinal image of the individual to the reference data.

In some embodiments, the method can further include determining a likelihood of a severity of the retinal disease based on the comparison of the number of occurrences of each of the key image features in the retinal image of the individual to the reference data. Although some examples described in this specification use a specific number of severity levels, such as four, the general concepts of the current invention are not limited to a particular number of severity levels. There could just be one level in some embodiments, i.e., detecting only, or there could be two, three, four, or even more than four severity levels in other embodiments.

In some embodiments, the processing of the retinal image of the individual to identify occurrences of each of the plurality of distinguishable image features includes applying a plurality of image operators to the retinal image. In some embodiments, the image operators can be, but are not limited to, at least one of a Laplacian of Gaussian (LoG), a Difference of Gaussian (DoG), a Determinant of Hessian (DoH), a SURF (Speeded Up Robust Features), a SIFT (Scale Invariant Feature Transform), a Morphological-based feature detector, a Multi-scale feature detector, or a Corner detector, for example.

In some embodiments, the method can further include receiving non-image information regarding the individual. The determining at least one of the likelihood of the presence of the retinal disease or the likelihood of developing the retinal disease can be further based on the non-image information regarding the individual.

In some embodiments, the method can further include, prior to the providing reference data, generating the reference data based on processing a plurality of expert-classified retinal images that have been classified according to at least one of risk of developing a retinal disease, retinal disease type or retinal disease severity.

In some embodiments, the generating the reference data can include processing the plurality of expert-classified retinal images to identify occurrences of each of a plurality of distinguishable reference image features, identifying key image features corresponding to the plurality of expert-classified retinal images, and computing a frequency of occurrence of each of the key image features corresponding to each classification of the expert-classified retinal images. In some embodiments, the identifying key image features can use a statistical clustering process. In some embodiments, the identifying the key image features can use at least one of a K-means, Mean Shift, Expectation maximization or Support Vector Data Description process, for example.

The following is a list of retinal diseases to which this method could apply. However, applications of the current invention are not limited to only the listed retinal diseases.

1. Age related macular degeneration. Conditions including geographic atrophy from age-related macular degeneration and related conditions (e.g., retinal pigment epithelial abnormalities consistent with a pattern dystrophy); age-related macular degeneration including earlier stages consisting of drusen and other retinal pigment epithelial abnormalities, and advanced stages including the choroidal neovascular ("wet") form;
2. Diabetic retinopathy, including diabetic macular edema and associated conditions such as macular edema from a retinal vein occlusion;
3. Macular edema from other causes including post-surgical cystoid macular edema and retinal telangiectasis;
4. Vitreoretinal interface abnormalities, including epiretinal membrane, lamellar hole, macular hole, vitreomacular adhesion;
5. Retinal degenerations and associated conditions, such as retinitis pigmentosa;
6. Inflammatory lesions of the retina and choroid (such as multifocal choroiditis, cytomegalovirus [CMV] retinitis);
7. Ocular tumors and associated conditions, such as choroidal nevi, choroidal melanoma, and retinoblastoma; and
8. Schisis or detachment of the retina, such as central serous chorioretinopathy, retinal detachment, and retinoschisis.

Another embodiment of the current invention is directed to a computer-readable medium for detecting, and classifying severity of, a retinal disease using retinal images. The computer-readable medium has non-transitory computer-executable code which, when executed by a computer, can cause the computer to perform any one or more of the above-noted methods.

Figure 6:
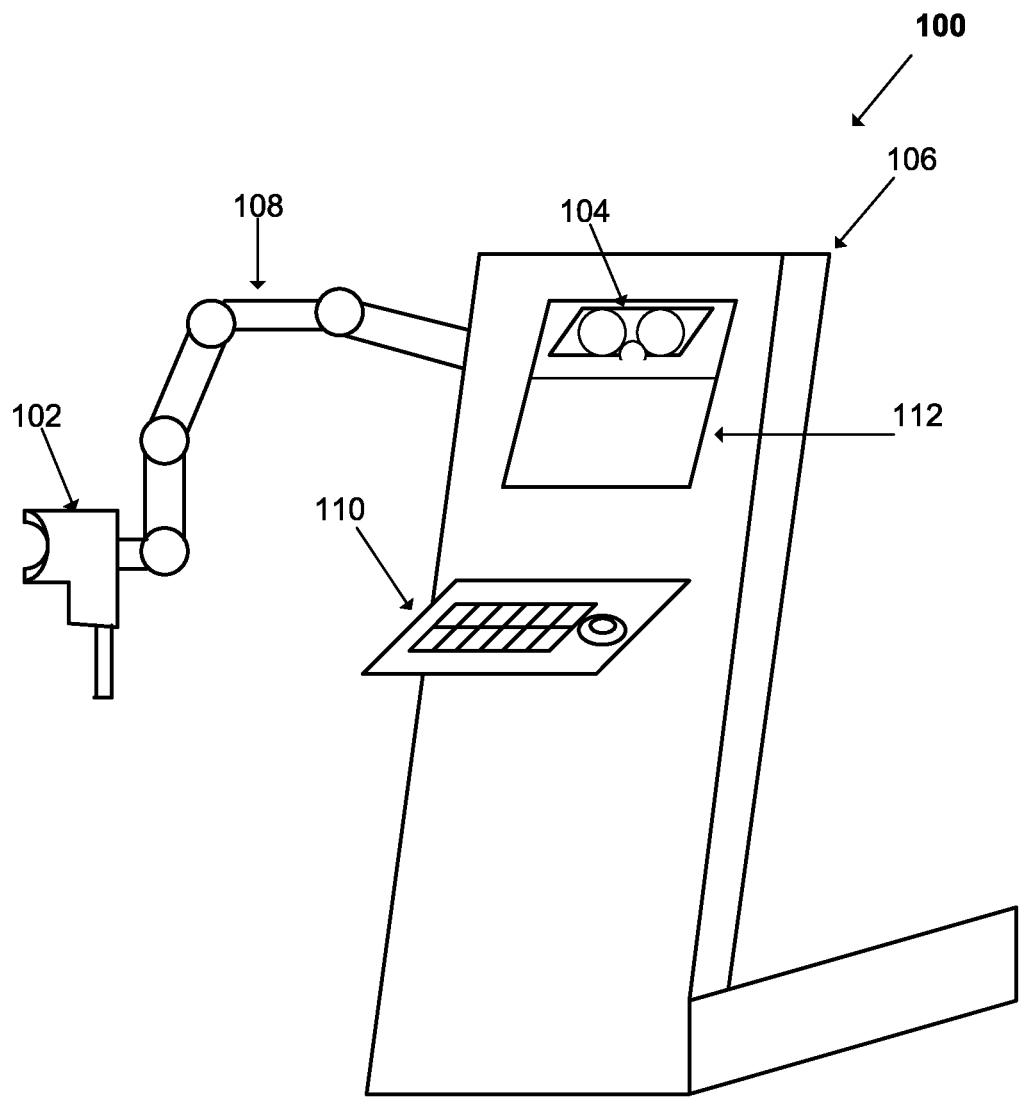
FIG. 6 is a schematic illustration of a system for detecting, and classifying severity of, a retinal disease according to an embodiment of the current invention.

FIG. 6 is a schematic illustration of a system 100 for detecting, and classifying severity of, a retinal disease according to an embodiment of the current invention. The system 100 has a retinal scanner 102 constructed to obtain retinal images of an individual, and a data processing system 104 in communication with the retinal scanner 102. The data processing system 104 can be or can include a computer, for example. For example, it can include one or more central processing units (CPUs) and/or graphics processing units (GPUs), can include memory and can include data storage devices, for example. It can also be a networked device, which can include devices connected over the Internet, for example. The data processing system 104 is configured to perform at least one of the methods of the current invention. It can be configured through hardware, such as, but not limited to ASICs and/or FPGAs, and/or can be programmed. When programmed, it can be embedded software and/or software obtained from a computer readable medium and/or received over a communications connection, for example.

In some embodiments, the system 100 can be, but is not limited to, a kiosk that could be set up in user-friendly locations such as doctors' offices, drugstores, grocery stores, motor vehicle administrations, safety for offices associated with occupations requiring minimal or no retinal pathology (military, surgeons, radiologists, pathologists, commercial transportation personnel such as truckers, pilots, taxi drivers), malls, etc. In an embodiment, the system 100 can be a kiosk that has an upright stand 106 designed to house all the required components (e.g., fundus imager, computer, input/output devices). The retinal scanner 102 can include a lens mask, forehead support and chin rest, for example. In some embodiments, the retinal scanner 102 can also include an adjustable arm 108 which could accommodate various users heights, for example. The system 100 can also include an input device 110 which can allow a patient to input data into the system. The input device could be, for example, a keyboard, mouse, touchpad, microphone, or any other suitable input device. Data could include individual's name, address, demographic information, history of illnesses, etc. The system 100 can also include also include one or more data output devices such as a video screen 112 (e.g., but not limited to, an LCD display). In some embodiments, the video screen 112 can provide, for example, an echo of the input from 110, patient instructions and/or marketing.

Another embodiment of the current invention provides a method of detecting, and classifying severity of, a disease using physiological information. The method includes at least one of receiving, retrieving or generating reference data that includes information concerning occurrences of key features for each of a plurality of disease and disease severity conditions. The "visual word" concept described above can be thought of more generally as a "physiological information word", for example, in order to make a similar analogy. The method according to this embodiment includes receiving physiological information of an individual; processing the physiological information of the individual to identify occurrences of each of a plurality of distinguishable features throughout at least a portion of the physiological information; identifying which ones of the identified occurrences of the plurality of distinguishable features of the physiological information of the individual correspond to the key features of the reference data; calculating, based on the identifying, a number of occurrences of each of the key features in the physiological information of the individual; and determining at least one of a likelihood of a presence of a disease or a likelihood of developing a disease based on a comparison of the number of occurrences of each of the key features in the physiological information of the individual to the reference data.

Ophthalmology applications for methods and system according to some embodiments of the current invention can include:
Diagnostics
  Diagnosing retinal disease, including:
    Discerning between diseases (AMD vs diabetic retinopathy vs cancer vs non-pathological pigmentations vs etc . . . see above)
    Discerning variations or subconditions within a disease (i.e. dry vs wet/neovascular form of AMD, see above)

Discerning subcategories within a disease (e.g. geographic atrophy involving the center of the macula or outside of the center of the macula)

Prescreening for a Disease (e.g. Finding at Risk Individuals with Intermediate Stage AMD)
Self administered prescreening (i.e. Kiosk based devices)

Disease Severity
Discerning between different levels of severity of a disease (i.e. 1 to 4 in a 4-category AMD categorization)
Helping clinicians assess progress of a disease (i.e. Performing longitudinal studies)

Medium/Long Term Prediction/Prognosis
Prognosis and predicting outcome of the disease in 2 to 5 years (prognosis)

Other Modalities
Application to other modalities such as OCT, or any time of flight sensors such as ultrasound imaging
Application to combinations of modalities, multi-modality such as combination or OCT and fundus
Application to mydriatic or non-mydriatic fundus imaging
Application to finding quality of fundus or OCT image (prompting a recapture of the image if quality is poor)
Application to allow for daily or as needed evaluation of individuals requiring no change in the retina to perform occupation safely Expansions to Non-Image Features
The methods can seamlessly take into account non-image information including patient history, health status (Body mass index, weight, . . . ), demographics (ethnicity, age, . . . ), medications, supplements, etc. . . . .
This would be done in steps 7 in the training and testing phases by simply concatenating additional binary 'bits' (if binary information, e.g. smoker vs. non-smoker) or values (e.g. Body mass index, age, number of years smoking) of the patient features to the visual feature vector (computed in step 5 and 6).
This is seamlessly incorporated if anyone of the tree-based classification methods is used (e.g. Random forest, decision tree, etc. . . . )
If SVM is used, this is used in conjunction with normalization and whitening of the patient feature vector.

Expansion to Using Amsler Grid Response
The method can seamlessly take into account self-administered or clinician administered Amsler grid or other visual neurophysiology evaluations of functional vision.
Assessment as to whether the functional abnormalities are captured in a numeric scale and are added as another feature value in the feature vector in step 7

EXAMPLES

The following describes some examples according to an embodiment of the current invention. The broad concepts of the current invention are not limited to only these examples.

AREDS Dataset of Images

While the AREDS reports involved thousands of participants, a subset of 600 subjects was selected by the National Institutes of Health (NIH) for genome studies. These consisted of 200 control patients, 200 neovascular AMD cases, and 200 geographic atrophy AMD cases[21]. These patients were followed over several years (median of 6.5 years and up to a total of 12 years) during which time a number of patients evolved to the more advanced stages. A dataset consisting of additional information on these 600 patients, including fundus photographs, was made publicly available by the NIH. This dataset is known as the AREDS dbGAP. A set of fundus photographs were digitized from 595 of these 600 patients forming a set of over 72,000 images graded for AMD severity[21,22,23,24]. For each patient and for each examination, several fundus photographs were taken of the left and right eyes. In particular, for each eye, left and right stereo pairs were taken for three fields of view: field 1M (centered on the temporal margin of the disc), field 2 (centered on the macula), and field 3M (centered temporal to the macula). Of these 595 participants with available fundus imagery, only 527 consented to reveal their AMD categories. Of all the retinal images available for these 527 participants, only field 2 images were used in the examples in this specification because they are centered on the macula, resulting in 11,344 images in all. From all these images, an additional selection process (explained below) was used to create a subset of good quality images for our examples. This resulted in 4,205 images, corresponding to 476 unique patients from the aforementioned 527 patients. From this set of images, when two stereo images of the same eye of the same patient on the same visit were present, we only kept the one classified as better quality (in order to remove what was for our purposes essentially redundant data). This resulted in a final number of 2,772 images that were used in our examples to train and test our AMD severity classifier algorithm. It should be noted that the good quality image selection step may have eliminated one right image, but not the corresponding left image of a stereo pair for some eyes, or vice versa (i.e. the right stereo image may have been classified as bad quality but the left was classified as good, or vice versa). Consequently, it is possible for the final number of images (2,772) to be greater than half of the set from which it was derived (4,205). The above mentioned numbers of images and corresponding patients are summarized in Table 1.

TABLE 1

Number of images and corresponding unique patients available in our study after (a) considering only patients who consented to release their AMD categories, (b) additional selecting for good quality images and (c) removing redundant stereo image from possible stereo image pairs.

| Field + Steps | Patients | Images |
| --- | --- | --- |
| Field 2 | 595 | 12401 |
| Field 2 (patients consenting to release categories) | 527 | 11344 |
| Field 2 (post quality check) | 476 | 4205 |
| Field 2 (post elimination of stereo pairs) | 476 | 2772 |

In addition to the field 2 images, database tables provided by the NIH list the level or category of AMD severity associated with each image. Specifically, each image is assigned an AMD category from 1 to 4, with 1 representing images showing minimal to no evidence of AMD; category 2 corresponding to the early stage of AMD[25]; category 3 corresponding to the intermediate stage of AMD; and category 4 representing images from patients with the advanced stage of AMD. FIG. 1 shows a typical example for each of the four AMD severity categories.

Classifications Problems

For the purpose of the following examples, we evaluated the performance of the algorithm based on several two-class problems among the various AMD categories: (a) {1 & 2} vs. (3 & 4); (b) {1 & 2} vs. (3); (c) (1) vs. {3}; (d) {1} vs. {3 & 4}, and one three-class classification problem: {1 & 2} vs. {3} vs. {4}. These problems were structured so as to discriminate between intermediate stage individuals, for whom treatment would help to maintain vision at a useful level, and other individuals that were either not at risk or too advanced. It was judged appropriate to cluster category 2 with category 1 since both categories have little clinical relevance to the risk of the need for monitoring for the advanced stage of AMD or the need to consider dietary supplements compared with either category 3 or 4.

Selection of Good Images

As is customary in ARIA processing for detection of AMD or diabetic retinopathy, a first step is applied to select good quality images[30,31]. From the initial dataset, only 'good quality' images are retained. In our study, this was performed in two ways: manually and automatically. The automated selection of good quality images is essentially a problem of classifying images into good vs. poor images. For this classification, we have also used a visual words approach that is essentially identical to the approach we report earlier to classify fundus images into different levels of AMD severity, minus the spatial histogram generation step (since, unlike the AMD classification problem, the location of certain image features does not generally correlate with its quality). As should be noted, good vs. poor image classification was also used in[31]. We evaluated the performance of our good vs. poor image classifier on a dataset of 400 AREDS images that were manually ground-truthed as either 'good' or 'bad' using a 5-fold performance cross-validation. This approach resulted in specificity of 93.0%, a sensitivity of 94.5%, a PPV of 93.1%, and NPV of 94.4%, and an accuracy of 93.8%.

TABLE 2

Number of images and corresponding unique patients in each dataset.

| Set | # of unique patients | # of total images | images in category 1 | images in category 2 | images in category 3 | images in category 4 |
|---|---|---|---|---|---|---|
| EIPC[µ] | 468 | 2145 | 626 | 89 | 715* | 715* |
| MIPC[‡] | 476 | 2772 | 626 | 89 | 1107 | 950 |
| MS[†] | 236 | 384 | 180 | 13 | 113 | 78 |

*Depending on the test, this number may be lower in order to keep each "total class" equal. For example, in the problem of classifying categories {1} vs. {3} only 626 images would be used (selected randomly) from category 3, since the maximum number of images for category 1 is 626. Similarly, in the test {1 & 2} vs. {3 & 4}, 715 images would be selected randomly from categories 3 and 4, since the maximum number of images for categories 1 and 2 combined is 715 (a lower number than the maximum number of images for categories 3 and 4 combined, 2057.)
[µ]Datasets with equal number of images per class
[‡]Datasets with maximum number of images per class As shown in Table 2, the number of patients and images available for training and testing purposes is unequal among the four AMD categories. Because of this, the following cohorts were considered:

Dataset with Maximum Number of Images Per Class (Denoted MIPC).

A subset of automatically selected images of good quality where the number of images in each AREDS category was kept as large as possible.

Dataset with Equal Number of Images Per Class (Denoted EIPC).

A subset of automatically selected images of good quality where the numbers of images in each AREDS category was kept equal. Depending on the test, this number may be lower in order to keep the "total number in each class" equal. For example, in the test {1} vs. {3} only 626 images would be used (selected randomly) from category 3, since the maximum number of images for category 1 is 626. Similarly, in the test {1 & 2} vs. {3 & 4} 715 images would be selected randomly from categories 3 and 4, since the maximum number of images for categories 1 and 2 combined is 715 (a lower number than the maximum number of images for categories 3 and 4 combined, 2057.)

Dataset with Manually Selected Images (Denoted MS).

A much reduced subset of images that were selected manually deemed to be of 'good quality', without attempt at a full search or optimization.

Sensitivity and Specificity of Automated Classification Compared with Expert Fundus Grading The number of true positives (denoted TP), false positives (FP), true negatives (TN), and false negatives (FN) using our automated AMD severity classification method was compared with the expert fundus grading provided in the NIH database with respect to the following:

Sensitivity (also called probability of detection) is defined as TP/(TP+FN). (i.e. percentage of retinas correctly identified as having the AMD category of interest as determined by the expert fundus grading); specificity is defined as TN/(TN+FP) (i.e. percentage of retinas correctly identified as not having the AMD category of interest as determined by the expert fundus grading); positive predictive value (PPV), the probability that a retina identified as having the AMD category of interest actually has that classification as determined by the expert grading, is defined as TP/(TP+FP), and negative predictive value (NPV), the probability that a retina identified as not having the AMD category of interest is indeed not that category as determined by the expert fundus grading, is defined as TN/(TN+FN), and accuracy, the total percentage of retinas correctly categorized by the automatic algorithm as categorized by the expert fundus grading, is defined as (TP+TN)/(TP+FP+TN+FN).

Results obtained for the different regional retinal division schemes (as discussed in the histogram generation step of the algorithm) were compared. The AREDS regions are based on the scheme developed by the AREDS group[25]. It contains regions with radii equal to ⅓, 1, and 2 times the disk diameter. Alternatively, an equally spaced regional division was tested along with an unequal (termed 'broad') division that emphasized the size of the central region (as opposed to the smaller and more focused central region used in the AREDS division scheme). As seen in Table 3, the best performance was obtained for the 'broad' subdivision. By design, the field 2 images are centered near or on the macular region. The 'broad' approach guarantees the consistent inclusion of the macular region without having to determine exactly the macular location.

TABLE 3

Figure 3:
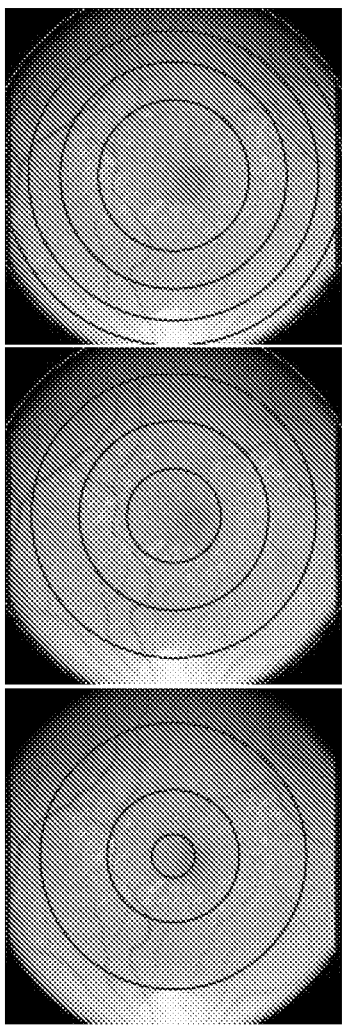
FIG. 3 shows the three grids tested: (left) grid based on AREDS specifications, (center) grid with equally spaced circles, and (right) custom grid with a large central circle near the macula.

Comparing performance results for the three grid schemes shown in FIG. 3 for the problem of classifying categories {1 & 2} vs. {3 & 4}, and using EIPC.

| Grid | Specificity | Sensitivity | PPV | NPV | Accuracy |
|---|---|---|---|---|---|
| AREDS | 92.3% | 91.3% | 92.3% | 91.4% | 91.8% |
| Regular | 92.9% | 91.3% | 92.8% | 91.5% | 92.1% |
| Broad | 95.4% | 95.5% | 95.4% | 95.5% | 95.5% |

Results of the two class classification problems are shown in Table 4, while Table 5 provides additional results in the form of a confusion matrix for the {1 & 2} vs. {3} vs. {4} classification problem. As can be seen from Table 4, the best results were obtained when image quality was determined manually (i.e. MS) as opposed to automatically. This underscores the importance of obtaining high quality fundus images. Comparison between EIPC and MIPC results did not show either approach as being clearly superior. Nevertheless, overall, EIPC did somewhat better than MIPC. Table 6 shows the results for the three class classification test. Again, the EIPC approach performed slightly better than MIPC, though it is worth noting that MIPC outperformed EIPC in classifying category 3.

TABLE 4

Performance results for the various two-class AMD severity classification problems.

| AMD category test | Set | Specificity | Sensitivity | PPV | NPV | Accuracy |
|---|---|---|---|---|---|---|
| {1 & 2} vs. {3 & 4} | EIPC | 95.4% | 95.5% | 95.4% | 95.5% | 95.5% |
|  | MIPC | 91.6% | 97.2% | 97.1% | 91.9% | 95.7% |
|  | MS | 98.4% | 99.5% | 98.4% | 99.5% | 98.9% |
| {1 & 2} vs. {3} | EIPC | 96.1% | 96.1% | 96.1% | 96.1% | 96.1% |
|  | MIPC | 95.7% | 96.0% | 97.2% | 94.0% | 95.9% |
| {1} vs. {3} | EIPC | 98.6% | 95.7% | 98.5% | 95.8% | 97.1% |
|  | MIPC | 96.3% | 96.8% | 97.9% | 94.5% | 96.7% |
| {1} vs. {3 & 4} | EIPC | 96.0% | 94.7% | 96.0% | 94.8% | 95.4% |
|  | MIPC | 95.4% | 97.7% | 98.6% | 92.3% | 97.1% |

TABLE 5

Performance results for the three-class AMD severity classification problem.

| AMD category test | Set | Accuracy | Confusion Matrix | | |
|---|---|---|---|---|---|
| {1 & 2} vs. {3} vs. {4} | EIPC | 91.8% | 89.23% | 7.27% | 3.50% |
|  |  |  | 11.33% | 86.43% | 2.24% |
|  |  |  | 0.28% | 0.00% | 99.72% |
|  | MIPC | 90.2% | 83.78% | 3.36% | 12.86% |
|  |  |  | 2.80% | 90.69% | 6.51% |
|  |  |  | 1.47% | 3.79% | 94.74% |

TABLE 6

Individual class performance results for the three-class AMD severity classification problem.

| Set | Class | Specificity | Sensitivity | PPV | NPV | Accuracy |
|---|---|---|---|---|---|---|
| EIPC | 1 & 2 | 94.2% | 89.2% | 88.5% | 94.6% | 92.5% |
|  | 3 | 96.4% | 86.4% | 92.2% | 93.4% | 93.1% |
|  | 4 | 97.1% | 99.7% | 94.6% | 99.9% | 98.0% |
| MIPC | 1 & 2 | 97.8% | 83.8% | 93.0% | 94.5% | 94.2% |
|  | 3 | 96.4% | 90.7% | 94.4% | 94.0% | 94.1% |
|  | 4 | 91.0% | 94.7% | 84.6% | 97.1% | 92.3% |

REFERENCES

1. Bressler, N. M. *Age-related macular degeneration is the leading cause of blindness*. JAMA, 2004. 291(15): p. 1900-1.
2. Bressler, N. M., Chang, T. S., Fine, J. T., Dolan, C. M., Ward, J. *Improved vision-related function after ranibizumab vs photodynamic therapy: a randomized clinical trial*. Arch Ophthalmol, 2009. 127(1): p. 13-21.
3. Chang, T. S., Bressler, N. M., Fine, J. T., Dolan, C. M., Ward, J., Klesert, T. R. *Improved vision-related function after ranibizumab treatment of neovascular age-related macular degeneration: results of a randomized clinical trial*. Arch Ophthalmol, 2007. 125(11): p. 1460-9.
4. *A randomized, placebo-controlled, clinical trial of high-dose supplementation with vitamins C and E, beta carotene, and zinc for age-related macular degeneration and vision loss: AREDS report no. 8*. Arch Ophthalmol, 2001. 119(10): p. 1417-36.
5. Bressler, N. M., Bressler, S. B. *Photodynamic therapy with verteporfin (Visudyne): impact on ophthalmology and visual sciences*. Invest Ophthalmol Vis Sci, 2000. 41(3): p. 624-8.
6. Age-Related Eye Disease Study (AREDS). Definitions of Final Age-Related Macular Degeneration (AMD) Phenotype Categories. Dec. 12, 2012]; Available from: http://www.ncbi.nlm.nih.gov/projects/gap/cgi-bin/GetPdf.cgi?id=phd001138.
7. Scotland, G. S., McNamee, P., Fleming, A. D. et al. *Costs and consequences of automated algorithms versus manual grading for the detection of referable diabetic retinopathy*. Br J Ophthalmol, 2010. 94(6): p. 712-9.
8. U.S. Department of Commerce, U.S.C.B. *The 2012 Statistical Abstract, The National Data Book*. Dec. 14, 2012]; Available from: http://www.census.gov/compendia/statab/2012/tables/12s0009.pdf.
9. Abramoff, M. D., Garvin, M. K., Sonka, M. *Retinal imaging and image analysis*. IEEE Rev Biomed Eng, 2010. 3: p. 169-208.
10. Smith, R. T., Nagasaki, T., Sparrow, J. R., Barbazetto, I., Klaver, C. C., Chan, J. K. *A method of drusen measurement based on the geometry of fundus reflectance*. Biomed Eng Online, 2003. 2: p. 10.
11. Brandon L., Hoover, A. *Drusen detection in a retinal image using multi-level analysis*, in Medical Image Computing and Computer-Assisted Intervention—MICCAI 2003, P. T. Ellis R E, Editor 2003, Springer Berlin Heidelberg: ? p. 618-625
12. Sbeh, B., Cohen Z. B., Mimoun L. D., Coscas G., Soubrane G. *An adaptive contrast method for segmentation of drusen*. in International Conference on Image Processing. 1997.
13. Rapantzikos, K., Zervakis, M., Balas, K. *Detection and segmentation of drusen deposits on human retina: potential in the diagnosis of age-related macular degeneration*. Med Image Anal, 2003. 7(1): p. 95-108.
14. Lee, N., Laine, A. F., Smith, T. R. *Learning non-homogenous textures and the unlearning problem with application to drusen detection in retinal images*, in 5th IEEE International Symposium on Biomedical Imaging: From Nano to Macro2008: Paris. p. 1215-1218.
15. Thdibaoui, A., Rajn, A., Bunel, P. *A fuzzy logic approach to drusen detection in retinal angiographic images*. in 15th International Conference on Pattern Recognition. 2000. Barcelona.
16. Checco, P., Corinto, F. *CNN-based algorithm for drusen identification*. in IEEE International Symposium on Circuits and Systems. 2006. Island of Kos.
17. Parvathi, S. S., Devi, N. *Automatic Drusen Detection from Colour Retinal Images*. in International Conference on Computational Intelligence and Multimedia Applications. 2007. Sivakasi, Tamil Nadu.
18. Karnowski, T. P., Govindasamy, V., Tobin, K. W., Chaum, E., Abramoff, M. D. *Retina lesion and microaneurysm segmentation using morphological reconstruction methods with ground-truth data*. Conf Proc IEEE Eng Med Biol Soc, 2008. 2008: p. 5433-6.

19. Santos-Villalobos, H., Karnowski, T. P., Aykac, D. et al. *Statistical characterization and segmentation of drusen in fundus images.* Conf Proc IEEE Eng Med Biol Soc, 2011. 2011: p. 6236-41.
20. Niemeijer, M., van Ginneken, B., Russell, S. R., Suttorp-Schulten, M. S., Abramoff, M. D. *Automated detection and differentiation of drusen, exudates, and cotton-wool spots in digital color fundus photographs for diabetic retinopathy diagnosis.* Invest Ophthalmol Vis Sci, 2007. 48(5): p. 2260-7.
21. National Eye Institute (NEI) Age-Related Eye Disease Study (AREDS). Dec. 12, 2012]; Available from: http://www.ncbi.nlm.nih.gov/projects/gap/cgi-bin/study.cgi?study_id=phs000001.v3.p1.
22. Ferris, F. L., Davis, M. D., Clemons, T. E. et al. *A simplified severity scale for age-related macular degeneration: AREDS Report No. 18.* Arch Ophthalmol, 2005. 123(11): p. 1570-4.
23. Davis, M. D., Gangnon, R. E., Lee, L. Y. et al. *The Age-Related Eye Disease Study severity scale for age-related macular degeneration: AREDS Report No. 17.* Arch Ophthalmol, 2005. 123(11): p. 1484-98.
24. *The Age-Related Eye Disease Study (AREDS): design implications. AREDS report no. 1.* Control Clin Trials, 1999. 20(6): p. 573-600.
25. *The Age-Related Eye Disease Study system for classifying age-related macular degeneration from stereoscopic color fundus photographs: the Age-Related Eye Disease Study Report Number 6.* Am J Ophthalmol, 2001. 132(5): p. 668-81.
26. Fei-Fei, L., Perona, P. *A Bayesian hierarchical model for learning natural scene categories in IEEE Computer Society Conference on Computer Vision and Pattern Recognition.* 2005.
27. Duda, R. O., Hart, P. E., Stork, D. G. *Pattern Classication and Scene Analysis* 1973, New York: John Wiley and Sons.
28. Jain, A. K. *Fundamentals of Digital Image processing* 1989: Prentice Hall.
29. Breiman, L. *Random forest.* Machine Learning, 2001. 45(1): p. 5-32.
30. Giancardo, L. *Quality Analysis of Retina Images for the Automatic Diagnosis of Diabetic Retinopathy, in Vision and Robotics (VIBOT)* 2008, Universit'e de Bourgogne.
31. Niemeijer, M., Abramoff, M. D., van Ginneken, B. *Image structure clustering for image quality verification of color retina images in diabetic retinopathy screening.* Med Image Anal, 2006. 10(6): p. 888-98.
32. Hubbard, L. D., Danis, R. P., Neider, M. W. *Brightness, contrast, and color balance of digital versus film retinal images in the age-related eye disease study 2.* Invest Ophthalmol Vis Sci, 2008. 49(8): p. 3269-82.

The embodiments discussed in this specification are intended to explain concepts of the invention. However, the invention is not intended to be limited to the specific terminology selected and the particular examples described. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of detecting, and classifying severity of, a retinal disease using retinal images, comprising:
   at least one of receiving, retrieving or generating reference data comprising information concerning occurrences of key image features for each of a plurality of retinal disease and disease severity conditions;
   receiving a retinal image of an individual;
   processing said retinal image of said individual to identify occurrences of each of a plurality of distinguishable image features throughout at least a region of interest of said retinal image;
   identifying which ones of said identified occurrences of said plurality of distinguishable image features of said retinal image of said individual correspond to said key image features of said reference data;
   calculating, based on said identifying, a number of occurrences of each of said key image features in said retinal image of said individual; and
   determining at least one of a probability of a presence of a retinal disease or a probability of developing a retinal disease based on a comparison of said number of occurrences of each of said key image features in said retinal image of said individual to said reference data,
   wherein said processing said retinal image of said individual to identify occurrences of each of said plurality of distinguishable image features comprises applying a plurality of image operators to said retinal image.

2. The method of claim 1, further comprising determining a probability of a severity of said retinal disease based on said comparison of said number of occurrences of each of said key image features in said retinal image of said individual to said reference data.

3. The method of claim 1, wherein said plurality of image operators includes at least one of a Laplacian of Gaussian (LoG), Difference of Gaussian (DoG), Determinant of Hessian (DoH), SURF (Speeded Up Robust Features), SIFT (Scale Invariant Feature Transform), Morphological-based feature detector, Multi-scale feature detector, or Corner detector.

4. The method of claim 1, wherein said retinal image of said individual is an optical image from a fundus camera.

5. The method of claim 1, wherein said retinal image of said individual is an optical coherence tomography image.

6. The method of claim 1, further comprising receiving non-image information regarding said individual, and
   wherein said determining at least one of said probability of said presence of said retinal disease or said probability of developing said retinal disease is further based on said non-image information regarding said individual.

7. The method of claim 1, wherein said generating said reference data comprises generating said reference data based on processing a plurality of expert-classified retinal images that have been classified according to at least one of risk of developing a retinal disease, retinal disease type and retinal disease severity by an expert.

8. The method of claim 7, wherein said generating said reference data comprises:
   processing said plurality of expert-classified retinal images to identify occurrences of each of a plurality of distinguishable reference image features,
   identifying key image features corresponding to said plurality of expert-classified retinal images, and
   computing a frequency of occurrence of each of said key image features corresponding to each classification of said expert-classified retinal images.

9. The method of claim 8, wherein said identifying key image features uses a statistical clustering process.

10. The method of claim 9, wherein said identifying key image features uses at least one of a K-means, Mean Shift, Expectation maximization or Support Vector Data Description process.

11. A computer-readable medium for detecting, and classifying severity of, a retinal disease using retinal images, said computer-readable medium comprising non-transitory computer-executable code which, when executed by a computer, causes the computer to:
at least one of receive, retrieve or generate reference data comprising information concerning occurrences of key image features for each of a plurality of retinal disease and disease severity conditions;
receive a retinal image of an individual;
process said retinal image of said individual to identify occurrences of each of a plurality of distinguishable image features throughout at least a region of interest of said retinal image;
identify which ones of said identified occurrences of said plurality of distinguishable image features of said retinal image of said individual correspond to said key image features of said reference data;
calculate, based on said identifying, a number of occurrences of each of said key image features in said retinal image of said individual; and
determine at least one of a probability of a presence of a retinal disease or a probability of developing a retinal disease based on a comparison of said number of occurrences of each of said key image features in said retinal image of said individual to said reference data,
wherein said processing said retinal image of said individual to identify occurrences of each of a plurality of distinguishable image features comprises applying a plurality of image operators to said retinal image.

12. The computer-readable medium of claim 11, wherein said non-transitory computer-executable code which, when executed by a computer, further causes the computer to determine a probability of a severity of said retinal disease based on said comparison of said number of occurrences of each of said key image features in said retinal image of said individual to said reference data.

13. The computer-readable medium of claim 11, wherein said plurality of image operators includes at least one of a Laplacian of Gaussian (LoG), Difference of Gaussian (DoG), Determinant of Hessian (DoH), SURF (Speeded Up Robust Features), SIFT (Scale Invariant Feature Transform), Morphological-based feature detector, Multi-scale feature detector, or Corner detector.

14. The computer-readable medium of claim 11, wherein said retinal image of said individual is an optical image from a fundus camera.

15. The computer-readable medium of claim 11, wherein said retinal image of said individual is an optical coherence tomography image.

16. The computer-readable medium of claim 11, wherein said non-transitory computer-executable code which, when executed by a computer, further causes the computer to receive non-image information regarding said individual, and
wherein said determining at least one of a probability of a presence of a retinal disease or a probability of developing a retinal disease is further based on said non-image information regarding said individual.

17. The computer-readable medium of claim 11, wherein said non-transitory computer-executable code which, when executed by a computer, further causes the computer to generate said reference data based on processing a plurality of expert-classified retinal images that have been classified according to at least one of risk of developing a retinal disease, retinal disease type and retinal disease severity by an expert.

18. The computer-readable medium of claim 17, wherein said generating said reference data comprises:
processing said plurality of expert-classified retinal images to identify occurrences of each of a plurality of distinguishable reference image features,
identifying key image features corresponding to said plurality of expert-classified retinal images, and
computing a frequency of occurrence of each of said key image features corresponding to each classification of said expert-classified retinal images.

19. The computer-readable medium of claim 18, wherein said identifying key image features uses a statistical clustering process.

20. The computer-readable medium of claim 19, wherein said identifying key image features uses at least one of a K-means, Mean Shift, Expectation maximization or Support Vector Data Description process.

21. A system for detecting, and classifying severity of, a retinal disease, comprising:
a retinal scanner constructed to obtain retinal images of an individual; and
a data processing system in communication with the retinal scanner, the data processing system configured to:
at least one of receive, retrieve or generate reference data comprising information concerning occurrences of key image features for each of a plurality of retinal disease and disease severity conditions;
receive a retinal image of said individual from said retinal scanner;
process said retinal image of said individual to identify occurrences of each of a plurality of distinguishable image features throughout at least a region of interest of said retinal image;
identify which ones of said identified occurrences of said plurality of distinguishable image features of said retinal image of said individual correspond to said key image features of said reference data;
calculate, based on said identifying, a number of occurrences of each of said key image features in said retinal image of said individual; and
determine at least one of a probability of a presence of a retinal disease or a probability of developing a retinal disease based on a comparison of said number of occurrences of each of said key image features in said retinal image of said individual to said reference data,
wherein said processing said retinal image of said individual to identify occurrences of each of a plurality of distinguishable image features comprises applying a plurality of image operators to said retinal image.

22. The system of claim 21, wherein said data processing system is further configured to determine a probability of a severity of said retinal disease based on said comparison of said number of occurrences of each of said key image features in said retinal image of said individual to said reference data.

23. The system of claim 21, wherein said plurality of image operators includes at least one of a Laplacian of Gaussian (LoG), Difference of Gaussian (DoG), Determinant of Hessian (DoH), SURF (Speeded Up Robust Features), SIFT (Scale Invariant Feature Transform), Morphological-based feature detector, Multi-scale feature detector, or Corner detector.

24. The system of claim 21, wherein said retinal scanner is a fundus camera and said retinal image of said individual is an optical image from said fundus camera.

25. The system of claim 21, wherein said retinal scanner is an optical coherence tomography scanner and said retinal image of said individual is an optical coherence tomography image.

26. The system of claim 21, wherein said data processing system is further configured to receive non-image information regarding said individual, and
wherein said determining at least one of a likelihood of a presence of a retinal disease or a likelihood of developing a retinal disease is further based on said non-image information regarding said individual.

27. The system of claim 21, wherein said data processing system is further configured to generate said reference data based on processing a plurality of expert-classified retinal images that have been classified according to at least one of risk of developing a retinal disease, retinal disease type and retinal disease severity by an expert.

28. The system of claim 27, wherein said generating said reference data comprises:
processing said plurality of expert-classified retinal images to identify occurrences of each of a plurality of distinguishable reference image features,
identifying key image features corresponding to said plurality of expert-classified retinal images, and
computing a frequency of occurrence of each of said key image features corresponding to each classification of said expert-classified retinal images.

29. The system of claim 28, wherein said identifying key image features uses a statistical clustering process.

30. The system of claim 29, wherein said identifying key image features uses at least one of a K-means, Mean Shift, Expectation maximization or Support Vector Data Description process.

31. A method of detecting, and classifying severity of, a disease using physiological information, comprising:
at least one of receiving, retrieving or generating reference data comprising information concerning occurrences of key features for each of a plurality of disease and disease severity conditions; receiving physiological information of an individual;
processing said physiological information of said individual to identify occurrences of each of a plurality of distinguishable features throughout at least a portion of said physiological information;
identifying which ones of said identified occurrences of said plurality of distinguishable features of said physiological information of said individual correspond to said key features of said reference data;
calculating, based on said identifying, a number of occurrences of each of said key features in said physiological information of said individual; and
determining at least one of a probability of a presence of a disease or a probability of developing a disease based on a comparison of said number of occurrences of each of said key features in said physiological information of said individual to said reference data,
wherein said processing said retinal image of said individual to identify occurrences of each of said plurality of distinguishable image features comprises applying a plurality of image operators to said retinal image.

* * * * *